United States Patent
Maggiore

(10) Patent No.: US 12,384,995 B2
(45) Date of Patent: Aug. 12, 2025

(54) INSERTABLE COMPONENTS FOR SINGLE-USE CONTAINERS

(71) Applicant: Sartorius Stedim Biotech GmbH, Goettingen (DE)

(72) Inventor: Frank Maggiore, Port Jefferson Station, NY (US)

(73) Assignee: Sartorius Stedim Biotech GmbH, Goettingen (DE)

( * ) Notice: Subject to any disclaimer, the term of this patent is extended or adjusted under 35 U.S.C. 154(b) by 1112 days.

(21) Appl. No.: 17/070,060

(22) Filed: Oct. 14, 2020

(65) Prior Publication Data
US 2021/0024867 A1     Jan. 28, 2021

Related U.S. Application Data

(63) Continuation-in-part of application No. 15/848,286, filed on Dec. 20, 2017, now abandoned.

(51) Int. Cl.
| | | |
|---|---|---|
| *C12M 1/00* | (2006.01) | |
| *C12M 1/06* | (2006.01) | |
| *C12M 1/09* | (2006.01) | |
| *C12M 1/36* | (2006.01) | |

(52) U.S. Cl.
CPC ............ *C12M 23/28* (2013.01); *C12M 23/14* (2013.01); *C12M 23/56* (2013.01); *C12M 27/02* (2013.01); *C12M 41/48* (2013.01)

(58) Field of Classification Search
CPC ...... C12M 23/14; C12M 23/56; C12M 23/28; C12M 23/26
See application file for complete search history.

(56) References Cited

U.S. PATENT DOCUMENTS

| | | |
|---|---|---|
| 3,328,255 A | 6/1967 | Ilg |
| 2002/0008389 A1 | 1/2002 | Nomura et al. |
| 2007/0263484 A1 | 11/2007 | Terentiev |
| 2009/0135667 A1 | 5/2009 | Terentiev |
| 2011/0013474 A1 | 1/2011 | Ludwig |
| 2011/0249526 A1 | 10/2011 | Wong |
| 2011/0310696 A1 | 12/2011 | Goodwin |
| 2012/0003733 A1 | 1/2012 | Gueneron |
| 2012/0175012 A1 | 7/2012 | Goodwin |
| 2015/0117142 A1 | 4/2015 | Staheli |
| 2015/0138913 A1 | 5/2015 | Jones |
| 2015/0265988 A1 | 9/2015 | Williams |
| 2016/0193576 A1 | 7/2016 | Larsen |
| 2021/0108169 A1* | 4/2021 | Petersen ............... C12M 41/00 |

FOREIGN PATENT DOCUMENTS

JP     2015232508 A   * 12/2015

* cited by examiner

*Primary Examiner* — Jonathan M Hurst
(74) *Attorney, Agent, or Firm* — Gerald E. Hespos; Michael J Porco

(57) ABSTRACT

An assembly includes a single-use sterilizable bag for containing a biological material. The single-use sterilizable bag has at least one insertion opening; and at least one insertable component configured to be inserted into the single-use sterilizable bag via the at least one insertion opening. The at least one insertable component includes a positioning unit for positioning the insertable component with respect to the single-use sterilizable bag and at least one of a processing unit and a sensing unit for handling the biological material.

16 Claims, 5 Drawing Sheets

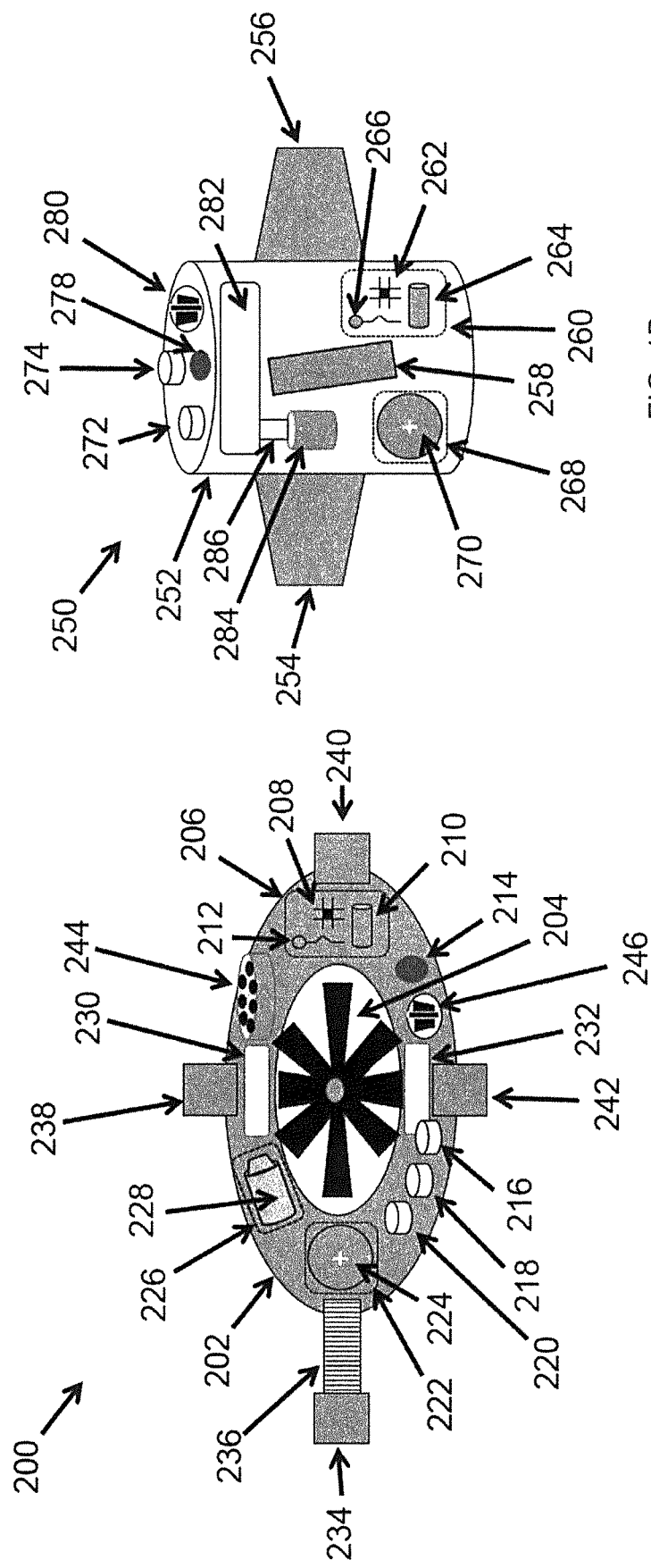

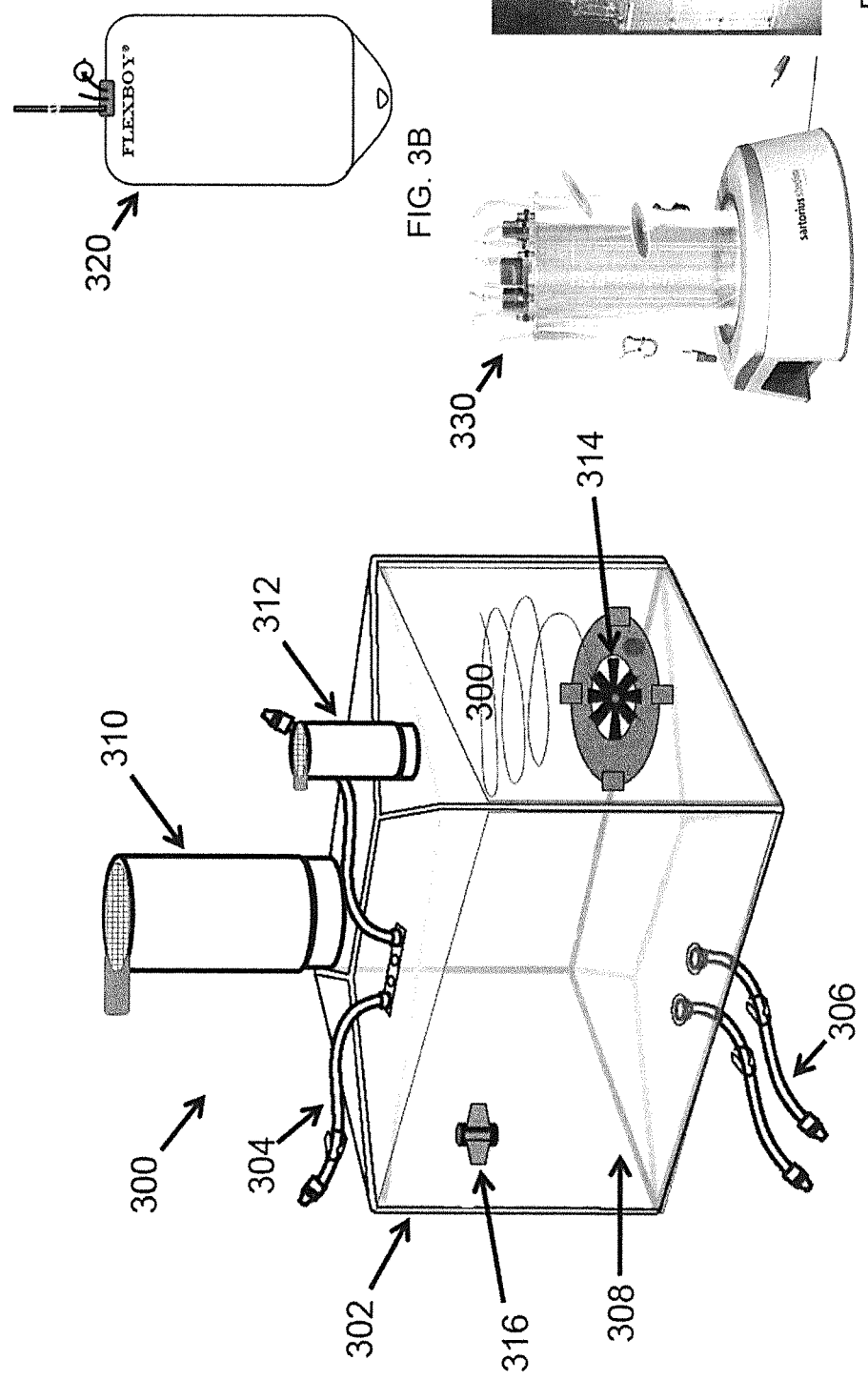

INSERTABLE COMPONENTS FOR SINGLE-USE CONTAINERS

The present application is a continuation-in-part application of U.S. patent application Ser. No. 15/848,286, filed Dec. 20, 2017, the contents of which are hereby incorporated by reference in their entirety.

BACKGROUND

Field of the Invention

The application relates to an assembly comprising a single-use sterilizable bag equipped with one or more insertable components for handling biological material as well as to a use thereof.

Description of the Related Art

A single-use container is a disposable container, i.e. a container that is discarded after being used. Single-use containers such as single-use bioreactor bags, mixing bags, and other fluid storage bags are widely used in the field of bioprocessing. Indeed, there are many setups, such as biopharmaceutical, pharmaceutical, laboratory, chemical, food and beverage, and industrial setups, that require a sterile environment as well as a sterile equipment in order to prevent any contamination of the products.

The advantages of single-use containers with respect to conventional stainless steel containers include flexibility, modularity, lower costs and reduced production time. Furthermore, a single-use system is easily sterilizable and helps reduce the risk of contaminations because of its disposability.

However, manufacturing such single-use containers involves the complex process of integrating mechanical, pneumatic, and electronic components into the single-use bags, which have to undergo sterilization. Further, the integration of these components in a particular configuration limits what the single-use bags may be utilized for, such as only fluid mixing or only fluid storage. This results in high-complexity manufacturing of customized single-use bags with a single purpose and functionality.

SUMMARY

According to one aspect, an assembly is provided. The assembly comprises: a single-use sterilizable bag for containing a biological material, wherein the single-use sterilizable bag comprises at least one insertion opening; and at least one insertable component configured to be inserted into the single-use sterilizable bag via the at least one insertion opening, wherein the at least one insertable component comprises: a positioning unit for positioning the insertable component with respect to the single-use sterilizable bag; and at least one of a processing unit and a sensing unit for handling the biological material.

According to another aspect, use of an insertable component with a single-use sterilizable bag for handling a biological material is described. The single-use sterilizable bag comprises at least one insertion opening and the insertable component comprises a positioning unit and at least one of a processing unit and a sensing unit. The insertable component is inserted into the single-use sterilizable bag via the at least one insertion opening, the insertable component is positioned with respect to the single-use sterilizable bag by means of the positioning unit, and the insertable component handles the biological material by means of the at least one of a processing unit and a sensing unit.

Details of exemplary embodiments are set forth below with reference to the exemplary drawings. Other features will be apparent from the description, the drawings, and from the claims. The drawings should be understood as exemplary rather than limiting, as the scope of the invention is defined by the claims.

BRIEF DESCRIPTION OF THE DRAWINGS

FIGS. 1A and 1B illustrate examples of insertable components that are suitable to be inserted into single-use containers for handling biological material.

FIGS. 3A through 3D illustrate different examples of single-use containers that can be combined with insertable components.

DETAILED DESCRIPTION

Figure 2A:
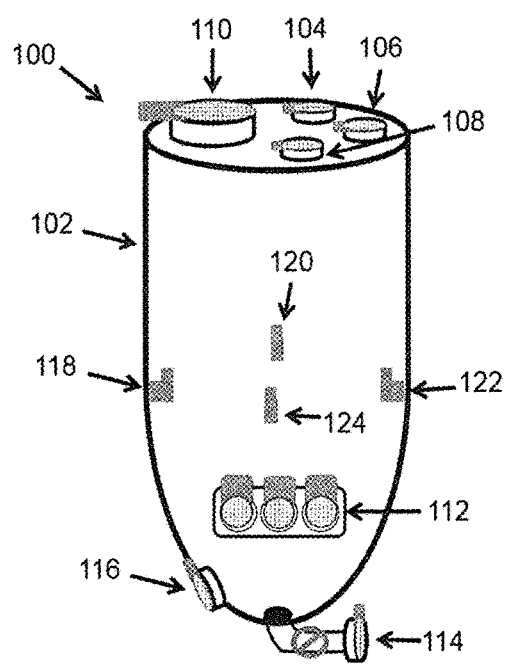
FIGS. 2A through 2I illustrate an examples of a single-use bioreactor bag with a plurality of insertable components inserted therein.

In the following text, a detailed description of examples will be given with reference to the drawings. It should be understood that various modifications to the examples may be made. In particular, one or more elements of one example may be combined and used in other examples to form new examples.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces. Herein, the phrase "coupled" is defined to mean directly connected to or indirectly connected with through one or more intermediate components. Such intermediate components may include both hardware and software-based components.

It will be appreciated by those skilled in the art that the block diagrams presented herein represent conceptual views of illustrative circuitry embodying the principles of the disclosure. Similarly, it will be appreciated that any flow charts, flow diagrams, state transition diagrams, pseudocode, and the like represent various processes which may be substantially represented in computer readable media and so executed by a computer or processor, whether or not such computer or processor is explicitly shown.

A single-use container is a disposable container that is configured for a one-time use. After the single-use container has been used once, it has fulfilled its function and may be disposed of. Exemplarily, a single-use container is made of plastic, which may include but is not limited to polyamide, polycarbonate, polyethylene, polystyrene, polyethersulfone, polypropylene, polytetrafluoroethylene, polyvinyl chloride, cellulose acetate and/or ethyl vinyl acetate. In one example, the single-use container may be rigid, i.e. its shape may not be modified. In another example, the single-use container may have flexible walls, i.e. it may be capable of changing its shape without breaking. In the following, the terms "single-use container" and "single-use bag" will be used interchangeably.

Exemplarily, a single-use container may comprise an enclosure with a multilayer film structure, i.e. a superposition of thin layers of plastic materials that provides a secure barrier between the content of the enclosure (e.g. biohazardous material) and the external environment. At the same time, the disposability reduces the requirements for cleaning and sterilization, as well as the potential for contaminations.

Single-use containers may be sterilized utilizing a validated sterilization process, e.g. by means of gamma irradiation and/or autoclaving. Exemplarily, the single-use bags may be provided pre-sterilized (e.g. before shipping) and/or may be sterilized upon or shortly before use (e.g. at or near the location of use) and/or after shipping.

Single-use containers may exemplarily be used for critical fluid handling applications in the biopharmaceutical and biomanufacturing industries, wherein a biological material must be handled. Biological materials may include materials comprising a biological system, such as cells, cell components, cell products, and other molecules, as well as materials derived from a biological system, such as proteins, antibodies and growth factors. Single-use bags may in addition contain other materials related to the biological material, e.g. supportive fluids such as nutrient rich media. Accordingly, in the following, the term "biological material" is used to include also such related materials, unless otherwise stated. Exemplarily, the biological material may be a fluid, e.g. a liquid.

The required manipulation of biological material for the purposes of a process may include but is not limited to storage, mixing, filtration, purification, centrifugation and/or cell cultivation. In order to perform one or more of the necessary actions, a simple single-use bag is combined with one or more insertable components that provide a specific functionality to the general bag. Specifically, the single-use bag is used to contain the biological material and the insertable components are used to handle the biological material. "Handle" may comprise processing (e.g. mixing) and/or performing measurements (e.g. of process parameters) on the biological material. In other words, the single-use bag can be produced as a simple container that has no mechanical, pneumatic, and electronic components integrated therein. The simple single-use bag is then configured for a specific use only later e.g. at the point of use by adding components that complete a specialized task e.g. for the manufacturing of biopharmaceutical and/or industrial products. As used herein, "simple bag" refers to a single-use sterilizable bag that has no or less components integrated therein as necessary in view of a functionality of the bag needed for a specified (predetermined or predeterminable) use e.g. at production time. In other words, a "simple bag" is not (yet) operational for the specified use and one or more additional components need to be provided or foreseen or implemented therein in order to become operational. Unless specified otherwise, single-use bags described in the following are simple bags.

Accordingly, there may be one or few standardized simple bag types from which, with modular construction, a whole variety of specialized bags for a particular function can be assembled at the location of usage. This results in lower costs for the large-scale manufacturing of simple single-use bags. Exemplarily, there may be only one type of simple bag, which can be combined with any kind of component capable of performing a specific task, such as a mixing device, a sensing device, or an aeration device. All necessary specialized bags may be derived from this all-purpose simple bag. In other examples, there may be more than one simple bag type. While all types may in principle be combined with any kind of insertable component, the types may differ from one another in that each type may be particularly suitable for one or more applications because of size and/or configuration. In any case, the number of standardized simple bag types is significantly lower than the number of specialized bags manufactured conventionally.

With the use of insertable components, the single-use bags have greater standardization, lower costs to manufacture, shorter lead times, higher ease of use, and greater flexibility. Such a modular assembly of single-use bag and component(s) allows for more innovation in the bag technology and faster rates of adoption for newer technologies e.g. in mixing and/or sensing modalities. Adding the insertable components, such as mixing devices, only at the location of use results also in prevention of bag puncture and/or leakage during shipping.

While the sterilizable bag is single-use, the insertable components may be used multiple times in different assemblies.

In order to allow the insertion of the insertable component(s), the single-use bag may contain one or more insertion openings. The single-use bag may comprise an internal volume (or chamber) enclosed by one or more external walls made of e.g. a plastic film. The insertable component may be transferred inside the internal volume of the single-use bag by means of an insertion opening in an external wall, e.g. a hole in the film.

The insertion opening may be configured to enable an aseptic transfer of the insertable component into the volume of the container. Exemplarily, the insertion opening may be provided with an aseptic connector. This may be necessary if e.g. the single-use bag and the insertable component are already sterile at the moment of insertion. An aseptic connector may comprise at least one membrane that covers the insertion opening to avoid contamination prior to inserting the component. When introducing the insertable component, the insertion opening may be covered by the insertable component itself in such a way that the membrane may be safely removed. For example, a transfer container as described below may be used for insertion. Alternatively, an aseptic transfer may be achieved by a thermoplastic or thermoweldable connection.

In another example, the single-use bag may be not sterile at the moment of insertion and the insertable component may be directly inserted in the internal volume through an exposed insertion opening. The single-use bag containing the insertable component may be then sterilized as a whole. The sterilization of the assembly will be discussed in detail below.

The single-use container may comprise a single insertion opening configured to let one or more insertable components through or it may comprise different insertion openings for different insertable components. Further, the single-use bag may comprise additional apertures in one or more walls for enabling connection to external elements e.g. input lines, output lines, communication lines. The additional apertures may exemplarily also be configured to provide aseptic connections e.g. by means of membranes.

As explained, thanks to the insertion opening an insertable component may be aseptically added to the single-use container at the point of use, providing the simple single-use bag with capabilities to handle the biological material it contains. In particular, the insertable component may comprise at least one of a processing unit and a sensing unit for handling the biological material.

A processing unit is configured to process the biological material, e.g. to interact with biological material in order to bring about a change in the material. In other words, the processing unit performs an action to the biological material, e.g. mechanically and/or chemically, and the material is modified by the processing. Examples of processing the material include but are not limited to mixing, filtration, purification, centrifugation and/or cell cultivation. Accordingly, the processing unit may e.g. be a mixing device, which mixes the contents of the single-use bag, or an aeration device, which pumps gas in the internal volume of the single-use bag. In some examples, the insertable component may comprise a single processing unit. In other examples, the insertable component may comprise more than one processing unit.

A sensing unit is configured to detect the conditions within the internal volume of the single-use bag and to perform measurements of parameters related to the process of interest. Exemplarily the sensing unit may measure temperature, pH, dissolved oxygen, cell viability, pressure, mixing speed and other quantities. Additionally or alternatively, the sensing unit may collect positional data, e.g. measure distance parameters to determine the position of the insertable component within the single-use bag. In some examples, the sensing unit may comprise a plurality of sensors, wherein each sensor may perform measurements of one or more parameters.

Once the simple single-use bag is provided with the insertable component, it becomes suitable for a specified use, i.e. it is capable of fulfilling its functionality as needed. For example, if the insertable component comprises a mixing device, the specified use of the bag may be mixing. If the insertable component can perform more than one operation, e.g. mixing with a mixing device and measuring temperature with a sensor, the specified use of the bag may be mixing and measuring the temperature. However, in some examples only one or some out of the range of capabilities of the insertable component may actually be used. Exemplarily, an insertable component that can mix and measure temperature may be used only for mixing or only for measuring the temperature.

The insertable component may comprise only a processing unit (or a plurality thereof), or only a sensing unit (or a plurality thereof), or both. In one example, the processing unit and the sensing unit may perform their actions autonomously, i.e., at least one controlling unit (e.g. internal to the insertable component) may be configured to control the operations of the processing unit without any input from the outside, i.e., from another device and/or from an operator. For example, the controlling unit may have software-controlled operational plans and/or one or more process steps that are automatically executed. The insertable component may comprise one controlling unit to control the processing unit and/or the sensing unit. The insertable component may further comprise a memory storage device. In other words, in some examples, the insertable component may be a drone-like element that acts autonomously. In particular, as described below, the insertable component may be capable of submerging itself in a fluid contained in the single-use bag, e.g. by means of the positioning unit.

It should be understood that a method of monitoring and/or controlling a process related to a biological material in the single-use bag may be implemented or executed, wholly or in part, by one or more processors of one or more controlling units in an insertable component. The one or more processors may execute instructions stored in one or more memories. The one or more processors may make determinations based on variables, configuration data, and/or other information stored in one or more memories (e.g., including look-up tables, setpoints, timing intervals and the like). In this manner, the controlling unit may control a processing unit without input from outside the single-use sterilizable bag or another device of the insertable component. For example, the controlling unit may control a processing device based on information stored in one or more memories, e.g. the controlling unit may start and stop a mixing device, i.e., a processing unit, based on start and stop times and/or an interval period stored in the one or more memories. As another example, the controlling unit may start and stop an aeration device, i.e., a processing unit, based on parameters stored in the one or more memories. As a further example, the controlling unit may control the sensing unit to measure a parameter, e.g., a temperature, over a predetermined period of time.

Additionally, the one or more processors may make determinations based on information (e.g., measurements) received from one or more sensors (e.g., temperature, pH, dissolved oxygen, cell viability, pressure, mixing speed and other quantities) of at least one sensing unit. In one embodiment, the controlling unit may control one or more processing units based on measurements received from at least one sensing unit. For example, the controlling unit may control the speed of a mixing device, i.e., a processing unit, based on the measured mixing speed received from the at least one sensing unit to maintain a mixing speed setpoint. As another example, the controlling unit may control a processing device based on whether a measured parameter as received from the sensing unit has exceeded a predetermined threshold, e.g., the controlling unit may stop operation of an aeration device upon the sensing unit measuring a threshold pressure inside the single-use sterilizable bag.

Furthermore, the one or more processors may make determinations based on calculations of the one or more processors. The one or more processors may control one or more processing devices in the insertable components based on determinations made by the one or more processors.

In another embodiment, at least one of the processing unit and the sensing unit may be controlled by an external device. Accordingly, the insertable component may comprise a communication unit that enables communication between the processing and/or sensing unit and the external device. The external device may operate the insertable component, e.g. send instructions to at least one of the processing unit and the sensing unit, exemplarily through the internal controlling unit. Additionally or alternatively the communication unit may be used to communicate in the other direction. Exemplarily, the sensing unit may send process data and/or positional data to the external device. In some examples, there may be more than one external device communicating with the insertable component for one or more purposes.

If a plurality of insertable components is present within the single-use bag, at least two of the insertable components may be provided with a communication unit that enables the insertable components to communicate with each other, e.g. to provide measurement data for tasks within a procedure and/or positional data for collision avoidance.

In some examples the operations of the insertable component may be partly performed autonomously and partly following instructions received from an external device.

The insertable component may further comprise a positioning unit for positioning the insertable component with respect to the single-use bag. It may be required that, after insertion, the insertable component be located in a specific position within the simple single-use bag, e.g. at a specified depth in the biological material in the form of a fluid. There may be a single designated position for a specific component or a plurality of possible positions. Constraints on the position may include the suitability of the position for performing the task for which the insertable component is configured and the avoidance of interference with other components within the single-use bag.

The positioning unit may comprise at least one dynamic element, i.e. configured to guide the movements of the insertable component, and/or at least one static element, i.e. configured to maintain the insertable component at a given position. Examples of dynamic elements include elements without an active propulsion source, such as baffles, and elements with an active propulsion source, such as an impeller with a motor. An example of a static element is a buoyancy device, which may be filled with a compressed gas to hold the position of the insertable component at a specified depth within the fluid.

In some examples, the single-use bag may comprise at least one attachment unit to which the insertable component can connect for maintaining position within the internal volume. The positioning unit may lead the insertable component e.g. by means of the dynamic element to the attachment unit. The insertable component may comprise a connecting unit configured to engage with the attachment unit of the single-use bag in order to anchor the insertable component to the attachment unit. For example, the connecting unit and the attachment unit may comprise a mechanical locking mechanism, such as protrusions and recesses that couple to each other.

In some examples, the connection between the attachment unit of the single-use bag and the connecting unit of the insertable component may also provide one or more sterile connections for the insertable component to the outside of the assembly, such as a fluid connection or a power connection. For example, a cable may be connected to the insertable component via the attachment unit.

The positioning unit may work autonomously, meaning that the insertable component may position itself with respect to the single-use bag without any external input. Alternatively, the positioning unit may be controlled by an external device e.g. via the communication unit. In other examples, the positioning of the insertable component may comprise both autonomous steps and steps controlled by an external device.

The body (or housing) of the insertable component may be formed from a sterilizable, chemically compatible material, exemplarily a biocompatible single-use plastic material. The single-use sterilizable bag may be sterilized using a first sterilization method and the insertable component may be sterilized separately from the single-use bag using a second sterilization method, the second sterilization method being different from the first sterilization method. As mentioned, the single-use bag may be sterilized by gamma radiation. The insertable component, i.e. its body and all the units and elements, may be instead sterilized using chemical sterilization by vaporized hydrogen peroxide. The reason is that the insertable component may contain sensitive electronics that are susceptible to damage if gamma radiation is used.

Alternatively, the body of the insertable component, along with non-sensitive elements, may be sterilized using the first sterilization method. The insertable component may further comprise at least one compartmentalized container configured to enclose an element sensitive to the first sterilization method. Herein "sensitive to a sterilization method" is used to indicate that an element subjected to the given sterilization method would be damaged.

The at least one compartmentalized container may be sterilized using a second sterilization method different from the first sterilization method and then be embedded in the insertable component after sterilization by being aseptically inserted therein.

For example, the body of the insertable component may be sterilized by gamma radiation and the sensitive elements (e.g. batteries) within the compartmentalized containers may be sterilized using an alternative method, e.g. chemical sterilization, and then aseptically inserted into the insertable component. Accordingly, the insertable component may comprise one or more compartmentalized containers that contain the sensitive elements, wherein the containers are sterilized using the alternative method and then embedded aseptically into the body of the insertable component. In some examples, such compartmentalized containers may contain non-sterile components that are wrapped by sterilizable material, so that e.g. a non-sterile processor may be inserted into a container, which then undergoes chemical sterilization to sterilize the surface of the external container. Alternatively, the non-sterile components may be expertly inserted into a compartment and/or chamber within the body of the insertable component and enclosed from the rest of the unit in a fluid tight enclosure.

The compartmentalized containers containing e.g. a motor or batteries may be re-used multiple times (i.e. in multiple insertable components) in order to reduce the cost of operation, since they can be extracted from and embedded into the insertable components.

FIGS. 1A and 1B illustrate examples of insertable components in line with what described above, which are suitable to be inserted into single-use containers for handling biological material.

FIG. 1A is a top view of an insertable component 200 containing a body 202 formed from a sterilizable material, for example a compatible plastic that may undergo multiple sterilization cycles. The body 202 of the insertable component 200 may comprise at least one mixing device 204 as processing unit, at least one power assembly 224, at least one controlling unit 208, 210, 212, at least one sensing unit with sensors 216, 218, 220, at least one motor assembly 228, at least one positioning unit 230, 232, 246, at least one indicator device 214, and at least one connecting unit 234, 238, 240, 242.

The controlling unit 208, 210, 212 may comprise at least one processor 208, at least one memory storage device 210, and at least one communication device 212. The communication device 212 is the communication unit of the insertable component 200. The functions of the controlling unit 208, 210, 212 may be provided through the use of dedicated hardware as well as hardware capable of executing software in association with appropriate software. In one embodiment, some or all of the functions may be performed by at least one processor 208, such as a computer or an electronic data processor, digital signal processor or embedded microcontroller, in accordance with code, such as computer program code, software, and/or integrated circuits that are coded to perform such functions, unless indicated otherwise. When provided by a processor 208, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, read only memory (ROM) for storing software, random access memory (RAM), and non-volatile storage. Other hardware, conventional and/or custom, may also be included in the controlling unit 208, 210, 212, such as a memory 210, input/output interfaces, a wireless transceiver, analog-to-digital converters, etc. It is to be appreciated that the controlling unit 208, 210, 212 may be coupled to the sensing unit and processing unit by hardwired and/or wireless means.

The power assembly 224 may comprise at least one power source such as a battery device to power the insertable component 200. The at least one power assembly 224 may receive power from an external source such as from a wired and/or wireless power source. The power source may come from a wired connection through the connecting unit 234 when engaged with an attachment unit of the single-use container, as described below.

The motor assembly 228 may comprise an electric motor that causes the rotation of the mixing device 204, i.e., the processing unit. The at least one mixing device 204 may be an impeller that may be formed into a plurality of shapes and designs to optimally support the mixing of the fluid material.

The insertable component 200 may contain a series of compartmentalized containers 206, 222, 226. Elements sensitive to a sterilization method (e.g. gamma radiation) such as the electronics, batteries, sensors, and motors may be sterilized utilizing an alternative method such as chemical sterilization and/or autoclaving and aseptically inserted into and/or connected to the insertable component 200 via the compartmentalized containers. Exemplarily, the compartmentalized containers 206, 222, 226 may contain the controlling unit 208, 210, 212, the power assembly 224 and the motor assembly 228 respectively.

The compartmentalized containers 206, 222, 226 may be connected to the body 202 through aseptic connections (not shown) in a sterilized transfer container (not shown), which may be expertly positioned to embed and/or connect to the insertable component body 202. It is possible that such assembly containers may contain non-sterile components that are wrapped by sterilizable material, such as a non-sterile processor 208, which may be inserted into a compartmentalized container that then undergoes chemical sterilization to sterilize its external surface. The compartmentalized containers 206, 222, 226 may be re-used multiple times to reduce the cost of operation.

Alternatively, non-sterile components may be expertly inserted into a compartment and/or chamber within the body 202 and enclosed from the rest of the unit in a fluid tight enclosure.

The insertable component 200 may comprise a sensing unit comprising a plurality of sensors 216, 218, 220 such as for the measurement of process parameters of the biological material inside the single-use bag container. The plurality of sensors 216, 218, 220 may perform measurements of temperature, pH, dissolved oxygen, cell viability, pressure, mixing speed, and other desired measurements.

Accordingly, the insertable component 200 comprises both a processing unit, i.e. the mixing device 204, and a sensing unit, i.e. the sensors 216, 218, 220.

The insertable component 200 may comprise the positioning unit 230, 232, 246 for positioning the insertable component 200 within an internal volume of a single-use bag filled with fluid. The positioning unit 230, 232, 246 may comprise an impeller 246 utilized for moving the insertable component 200 to a desired position. The positioning unit may additionally comprise buoyancy devices 230 and 232, which may be filled with a compressed gas to hold the desired position of the insertable component 200 at a specified depth within the fluid-filled volume. Alternatively, or additionally, the body 202 may be constructed of a material that makes the insertable component 200 buoyant at a particular depth.

In some examples, the mixing device 204 may also be utilized to position the insertable component 200 during the initial positioning for attachment with an attachment unit of a single-use bag (not shown). The mixing device 204 may perform a coarse positioning while the impeller 246 may be used to refine the positioning.

The insertable component 200 may comprise at least one connecting unit 234, 238, 240, 242 that may connect to an attachment unit internal to the single-use bag chamber. Each connecting unit may utilize an attachment mechanism to attach to the attachment unit on the bag. The connecting units 234, 238, 240, 242 may be pairwise located at opposite points of the insertable component 200 to provide stability to the attachment. At least one of the connecting units 234, 238, 240, 242 may be extendable in at least one direction, so that all connecting units can be properly attached and/or so that the insertable component 200 can hold a specific position within the single-use bag.

The insertable component 200 may comprise at least one indicator device 214 to provide an operator with visual information on the status of the insertable component 200, such as if it is working properly or if the battery level is low.

The insertable component 200 may additionally comprise another processing unit, such as a sparger device 244, which may provide compressed gases into the interior of the fluid-filled bag for aeration. The sparger device 244 may utilize a tubing line to receive the compressed gas, wherein the tubing line may go through one of the connecting units 234, 238, 240, 242 to the outside, or utilize a compressed gas container (not shown) within the insertable component 200.

The insertable component 200 may be inserted alone into a simple single-use bag and/or may work in collaboration with other insertable components. The plurality of insertable components may communicate with each other and/or to an external data communication device to coordinate their positioning and functioning within the single-use bag.

FIG. 1B is a side view of an insertable component 250 that comprises a body 252 formed from a sterilizable material, exemplarily a compatible plastic that may undergo multiple sterilization cycles.

The insertable component 250 may comprise at least one power assembly 270, at least one controlling unit 262, 264, 266, at least one sensing unit comprising sensors 272 and 274, at least one indicator device 278, and at least one positioning unit 254, 256, 258, 282, 280.

The controlling unit 262, 264, 266 may comprise a processor 262, a memory storage device 264, and a communication device 266. The functions of the controlling unit 262, 264, 266 may be provided through the use of dedicated hardware as well as hardware capable of executing software in association with appropriate software. In one embodiment, some or all of the functions may be performed by at least one processor 262, such as a computer or an electronic data processor, digital signal processor or embedded microcontroller, in accordance with code, such as computer program code, software, and/or integrated circuits that are coded to perform such functions, unless indicated otherwise. When provided by a processor 262, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, read only memory (ROM) for storing software, random access memory (RAM), and non-volatile storage. Other hardware, conventional and/or custom, may also be included in the controlling unit 262, 264, 266, such as a memory 264, input/output interfaces, a wireless transceiver, analog-to-digital converters, etc. It is to be appreciated that the controlling unit 262, 264, 266 may be coupled to the sensing unit and processing unit by hardwired and/or wireless means.

The power assembly 270 may comprise at least one power source such as a battery device to power the insertable component 250. As explained for the example of view A, the insertable component 250 may contain compartmentalized containers 260 and 268 for the sensitive elements such as the controlling unit 262, 264, 266 and the power assembly 270.

The insertable component 250 may comprise a sensing unit comprising a plurality of sensors 272 and 274 such as for the measurement of process parameters of the biological material inside the single-use bag container. Accordingly, the insertable component 250 comprises only a sensing unit, i.e. the sensors 272 and 274, and not a processing unit.

The insertable component 250 may comprise at least one indicator device 278 to provide an operator with visual information on the status of the insertable component 250, such as if it is working properly or if the battery level is low.

The at least one positioning unit 254, 256, 258, 282, 280 comprises a moving baffles assembly 254, 256, 258, a buoyancy device 282, and a propulsion device 280. The buoyancy device may contain at least one compressed gas from a compressed gas container 286, wherein the gas enters the at least one buoyancy device through at least one tubing. The baffles assembly 254, 256, 258 may be utilized to move within a fluid, particularly a fluid being mixed, without an active propulsion source. Alternatively, the propulsion device 280 may be utilized along with the baffles assembly 254, 256, 258 and the buoyancy device 282 to properly position the insertable component within fluid in the single-use bag and avoid collisions with other components and/or devices within the chamber.

The insertable component 250 may be inserted alone into a simple single-use bag and/or may work in collaboration with other insertable components. The plurality of insertable components may communicate with each other and/or to an external data communication device to coordinate their positioning and functioning within the single-use bag.

As previously discussed, one or more insertable components such as those shown in FIGS. 1A and 1B may be aseptically inserted in a single-use bag. Exemplarily, an insertable component may be inserted in a single-use container by means of a transfer container.

The transfer container may be a receptacle in which the insertable component may be enclosed. The transfer container may comprise an aseptic connector that may be connected to an aseptic connector of the single-use bag to create a secure, sterile connection in order to transfer the insertable component from within the transfer container to the inside of the single-use bag.

The transfer container may contain a scaffold for supporting the insertable component while inside, so that the insertable component may be exemplarily held above a filter membrane of the aseptic connector of the single-use bag prior to removal of the filter membrane. The scaffolding is to prevent the weight of the insertable component from puncturing, tearing, or removing the filter membrane from its attachment to the transfer container. The scaffold may exemplarily be made from a sterilizable plastic material, which may break when the filter membrane is removed from the aseptic connector but does not drop inside the single-use bag, as the insertable component instead does. The scaffolding design prevents components of the scaffolding and/or particulates from falling into the single-use bag potentially resulting in particulate contamination. The scaffold may be partially bonded to the filter membrane through an attachment mechanism such as heat welding/bonding, or it may utilize a secondary attachment mechanism attached to the filter membrane, i.e. it may be indirectly attached to the filter membrane. The transfer container may comprise a removal assembly which removes the scaffolding assembly when pulled or removed, and/or the removal of the scaffolding may occur through other attachment mechanisms during the aseptic connection. Alternatively or additionally the scaffolding may contain a latch mechanism which may be manually and/or automatically mechanically moved and/or altered to allow the insertable component to drop inside the single-use bag after the filter membrane is removed.

The transfer container may be sterilized together with the insertable component, e.g. via chemical sterilization by vaporized hydrogen peroxide.

After the insertable component is dropped from the transfer container into the single-use bag, the positioning unit of the insertable component positions it within the single-use container. Exemplarily, as mentioned, the positioning unit may lead the insertable component to an attachment unit to which it can connect via a connecting unit. The attachment unit may provide e.g. a wire or cable connection to provide power, fluids and/or data to the insertable component once it has been assembled together with the single-use bag.

FIG. 2A-2I illustrates an example of an assembly comprising a single-use bag 100 with a plurality of insertable components inserted therein. As shown in the figures, the assembly has a modular construction.

FIG. 2A is a front view of a single-use bag 100 formed from a sterilizable film material 102, exemplarily sterilized by gamma irradiation. The single-use bag 100 is a sterilizable plastic disposable container that is adapted to contain or hold at least one fluid and may exemplarily be a bioreactor bag.

The single-use bioreactor bag 100 may utilize supporting equipment (not shown) and a holding mechanism (not shown) to support the bioreactor bag. The single-use bioreactor bag 100 may comprise a plurality of aseptic connectors, such as an OPTA® connector, to connect tubing, filters, samplers, inputs, outputs, and for the sterile insertion of associated components and devices for the control and monitoring of the process. Alternatively, to the use of aseptic connectors, the single-use bioreactor bag 100 may utilize at least one thermoweldable length of tubing (not shown) which may be thermally welded to the assembly.

The single-use bioreactor bag 100 may comprise aseptic connectors 104 and 106 for aseptic tubing connections, aseptic connector 108 for small device insertion, and 110 for large device insertion. The single-use bioreactor bag 100 may comprise a sampling and sensor port 112 including a plurality of aseptic connectors. The single-use bioreactor bag 100 may comprise an outlet port 114 with at least one aseptic connector. The single-use bioreactor bag 100 may additionally comprise an aseptic connector 116 for inserting a sparger device.

The single-use bioreactor bag 100 may comprise an attachment unit including a plurality of attachment components 118, 120, 122 and 124. The attachment components are utilized to anchor an internal device such as an insertable component (not shown), as shown in FIG. 2F.

Figure 2B:
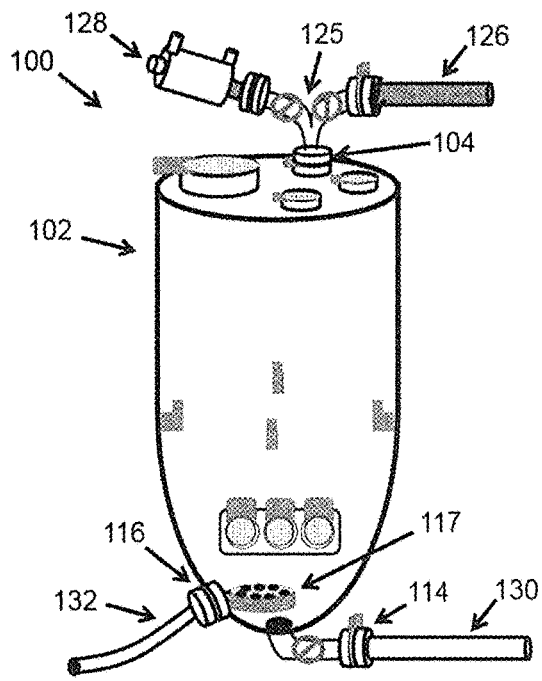

FIG. 2B is a front view of the single-use bioreactor bag 100 with a branched Y tubing 125 aseptically connected to the aseptic connector 104. The branched Y tubing 125 comprises an input tubing line 126 for the sterile introduction of media into the single-use bioreactor bag 100 chamber. The input tubing line 126 may comprise a sterilizing grade filter or other filter. The branched Y tubing 125 may comprise a vent filter 128 for the sterile venting of the single-use bioreactor bag 100, which may comprise a sterilizing grade filter or other vent filter.

The outlet port 114 of the single-use bioreactor bag 100 may be connected to a length of outlet tubing 130 with an aseptic connector. The outlet tubing 130 may remain in the closed state during filling and cell cultivation and/or fermentation.

The aseptic connector 116 may be utilized to connect and insert a sparger device 117 into the internal volume of the single-use bioreactor bag 100. The sparger device 117 may comprise a length of tubing which is connected to a filtered gas line, so that it can pump filtered compressed gas into the bioreactor chamber to aid in mixing and aeration. The sparger device 117 may comprise a plurality of holes in different configurations for mixing and aeration.

Figure 2C:
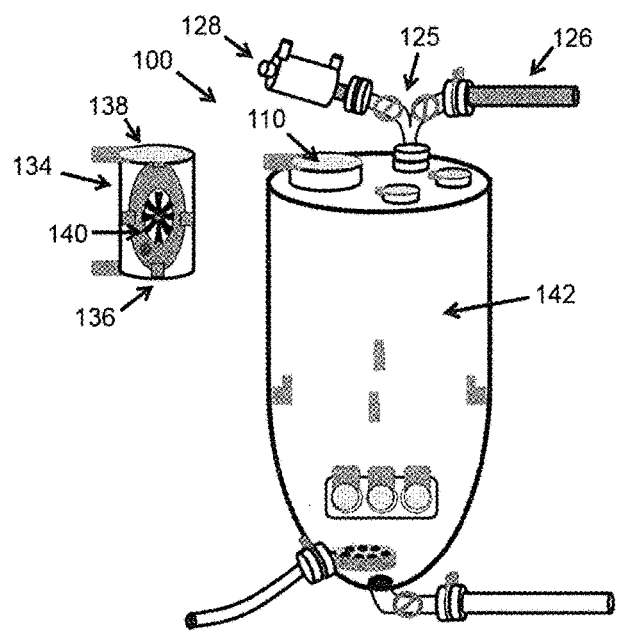

FIG. 2C is a front view of the single-use bioreactor bag 100 filled with a filtered nutrient rich media 142 through the inlet tubing assembly 126. The vent filter 128 equalizes the pressure of the single-use bioreactor bag 100 with the external environment during filling.

At least one insertable component 140 may be prepared for connection in a sterilized transfer container 134, which may be connected to the single-use bioreactor bag 100 by means of at least one aseptic connector 136 and the device insertion port aseptic connector 110. An additional aseptic connector 138 may be available in the transfer container to connect an additional sterilized transfer container (not shown) containing at least one additional insertable component (not shown). The insertable component 140 may exemplarily be the one shown in FIG. 1A.

The insertable component 140 may be supported within the transfer container 134 with a scaffold (not shown) to hold it above the filter membrane of the aseptic connector 136 and/or 138. The scaffold (not shown) is exemplarily made from a sterilizable plastic material which breaks when the filter membranes are removed from the connected aseptic connector. The scaffold does not drop into the single-use bioreactor bag 100. The insertable component 140, alternative/additional insertable components (not shown), and the transfer container 134 may be sterilized utilizing the same and/or different sterilization method as that of the single-use bioreactor bag 100. For example the single-use bioreactor bag 100 may be sterilized by gamma irradiation while the sensitive electronics within the insertable component 140 may be susceptible to damage utilizing such a method, so that chemical sterilization by vaporized hydrogen peroxide may be utilized for the insertable component and the transfer container 134 instead. Alternatively, the insertable component 140 may be sterilized via the same method as the single-use bioreactor bag 100, such as gamma irradiation. The sensitive elements such as the electronics, batteries, and motor devices may be sterilized utilizing an alternative method such as chemical sterilization and/or autoclaving and then aseptically inserted into the insertable component 140 through aseptic connections (not shown) in the transfer container 134, which are expertly positioned to embed and/or connect to the insertable component 140.

Figure 2D:
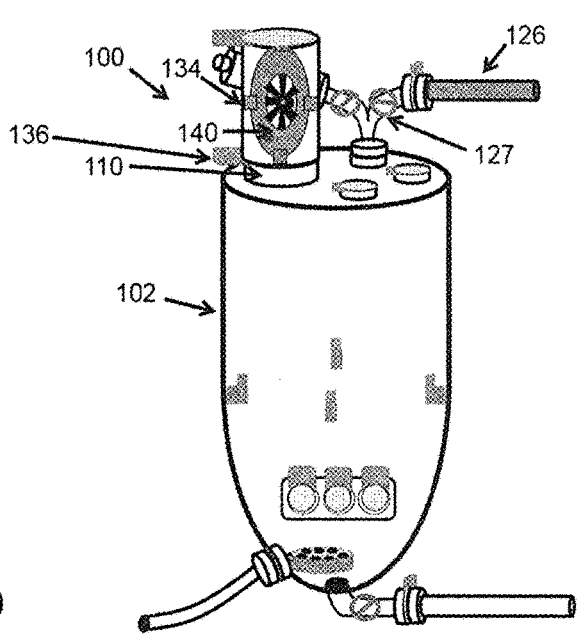

FIG. 2D is a front view of the single-use bioreactor bag 100, wherein the filling step has been completed and the inlet tubing assembly 126 line is clamped off utilizing clamp 127. The insertable component 140 inside the sterilized transfer container 134 is connected to the single-use bioreactor bag 100 by connecting the aseptic connector 136 to the device insertion port aseptic connector 110.

Figure 2E:
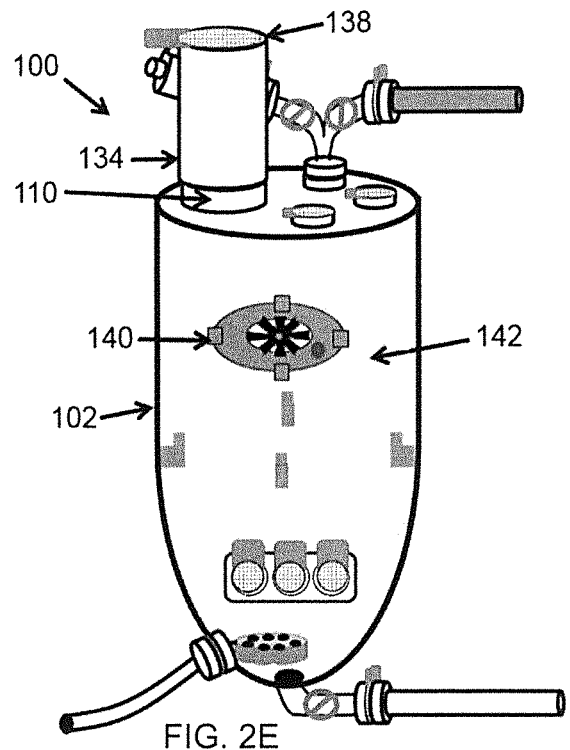
Figure 2F:
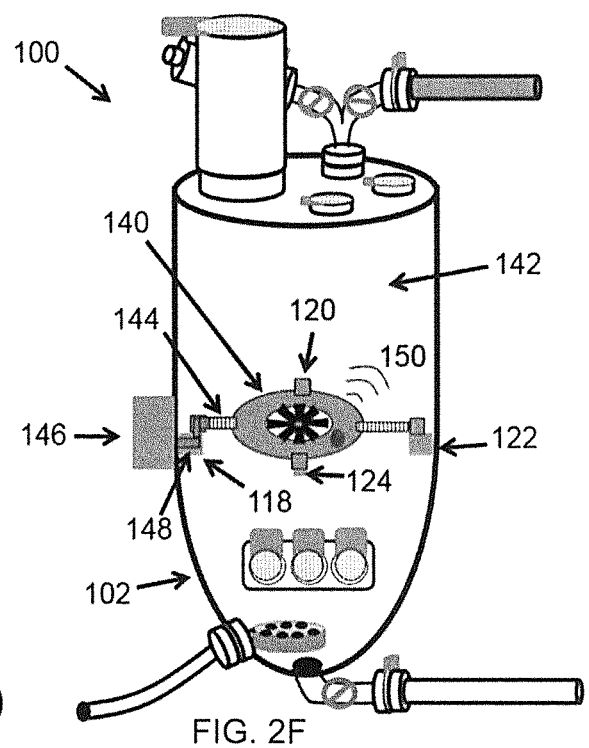

FIG. 2E is a front view of the single-use bioreactor bag 100 where the aseptic connection is completed by removing the filter membranes between the connections of aseptic connectors 110 and 134. The scaffolding (not shown) holding the insertable component 140 in place is broken but does not break into the single-use bioreactor bag 100. The insertable component 140 drops into the biological material, i.e. the nutrient rich media 142 within the envelope of the single-use bioreactor bag 100. The insertable component 140 may utilize the mixing device and the positioning unit to position itself within the fluid-filled internal volume of the single-use bioreactor bag 100.

FIG. 2F is a front view of the single-use bioreactor bag 100 where the insertable component 140 positions itself near the attachment components 118, 120, 122, 124. The insertable component 140 attaches to at least one of the attachment components 118, 120, 122, 124 utilizing its connecting unit, which includes at least one arm 144 extendable in at least one direction. The at least one arm 144 is extended and attaches e.g. to the attachment component 118 utilizing at least one attachment method such as locking into place with at least one mechanical locking mechanism (not shown).

The at least one arm 144 may additionally be utilized to connect a wire, cable, and/or other means 148 to provide power and data communication to the insertable component 140. An external connection box 146 may be located external to the single-use bioreactor bag 100, as part of the supporting equipment and holding mechanism to support the bioreactor bag. The external connection box 146 may bring power from at least one external source such as a wired plug, a battery, a solar cell, or other power source to the insertable component 140 utilizing a wire, cable, and/or other connection 148 through the attachment component 118. The external connection box 146 may additionally provide data communication from the insertable component 140 to an external processor and/or computing device and/or from an external processor and/or computing device to the insertable 140. The wire, cable, and/or other connection 148 may be a water-tight connection such as a NEMA connection.

Alternatively, the autonomous mixing device 140 may communicate data through a wireless method such as through a wireless electronic method e.g. WiFi or Bluetooth, or active RFID/NFC communication, through an optical method such as using light, a screen display, and/or infrared LEDs, through a sonic method such as with sound waves, ultrasound, and/or infrasound, or through some other contactless communication method. The use of an antenna (not shown) may be utilized to extend the range of the wireless signal 150 through the fluid 142. Alternatively, the insertable component 140 may have a wired connection (not shown) through the transfer container 134 to provide power and/or data communications within the single-use bioreactor bag 100.

Figure 2G:
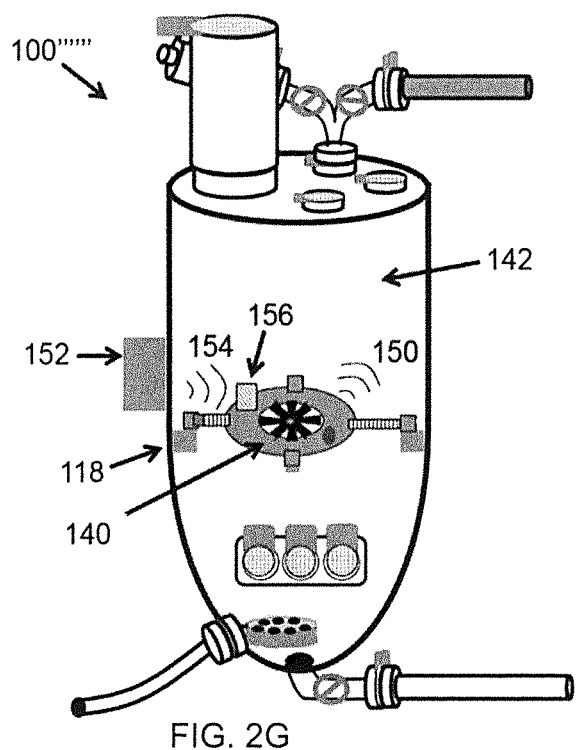

FIG. 2G is a front view of an alternative example for the single-use bioreactor bag 100, wherein the insertable component 140 utilizes a wireless power method 154 for prolonged usage of the component during the cell culture and/or fermentation process. The wireless power may come from an external induction power device 152 on the insertable component 140 or through the at least one arm 144. Alternatively, an external laser- or light-generating device (not shown) transmits optical power to an internal receiver, such as a solar cell or other conversion device (not shown) on the insertable component 140 or through the at least one arm 144. Alternatively, another wireless power source may be utilized. Such a wireless power device would be expertly formed to minimize the distance of the wireless power transmitter and the wireless power receiver to reduce any power losses due to the transmission of power through a fluid. In alternative examples, the insertable component 140 may comprise an onboard battery capable of providing the required power for the duration of the batch run.

Figure 2H:
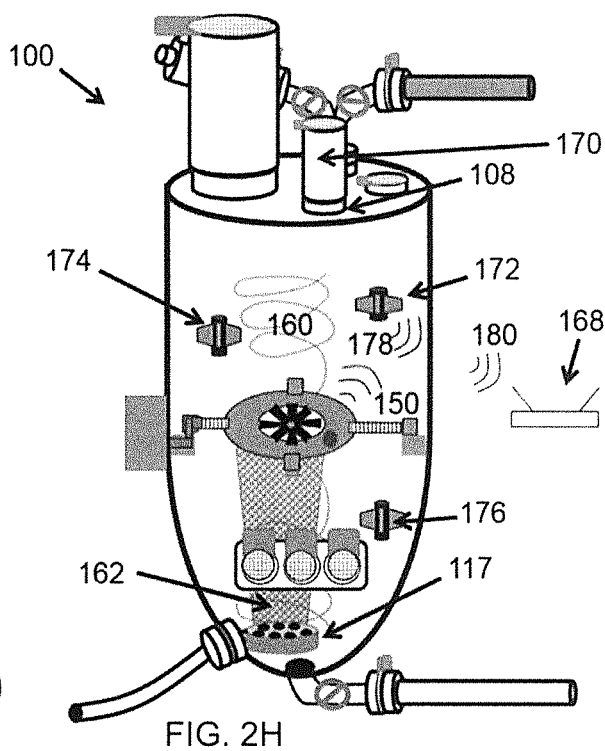

FIG. 2H is a front view of the single-use bioreactor bag 100 wherein the insertable component 140 may utilize its mixing device for mixing 160 the fluid 142. The insertable component 140 may comprise at least one mixing impeller (not shown) with a plurality of shapes and designs. The insertable component 140 may operate at a certain revolutions per minute (RPM) and tip speed to mix a fluid thoroughly or for the growth of cells within the fluid container. Additionally, the insertable component 140 may incorporate at least one sensing unit (not shown). The sparger device 117 may activate and properly aerate 162 the fluid 142 within the chamber with a specific gas concentration at a measured rate.

A plurality of insertable components 172, 174, 176, each with their own functionalities (e.g. comprising different sensors), may be aseptically inserted into the single-use bioreactor bag 100. Exemplarily, each of the insertable components 172, 174, 176 may be the one shown in FIG. 1B. The plurality of insertable components 172, 174, 176 may utilize the positioning units, such as the movable baffles device, to move within the current of the mixing 160 and to avoid getting stuck in the primary impeller of the insertable component 140.

The plurality of insertable components 172, 174, 176 may communicate with a wired and/or wireless connection 178 to each other and/or to an external communication device 168 (e.g. via wireless signal 180) to coordinate the motion relative to one another to avoid collisions and/or for sampling coordination purposes. The plurality of insertable components 172, 174, 176 may be aseptically inserted into the bioreactor bag through at least one device insertion port 108 via a transfer container 170 containing aseptic connectors as previously shown.

The plurality of insertable components 172, 174, 176 may comprise additional sensor functionalities compared to the insertable component 140. These sensors (not shown) may additionally sample different areas of the fluid-filled bag chamber. The external communication device may receive sensor data from the plurality of insertable components 172, 174, 176 as well as from insertable component 140.

Figure 2I:
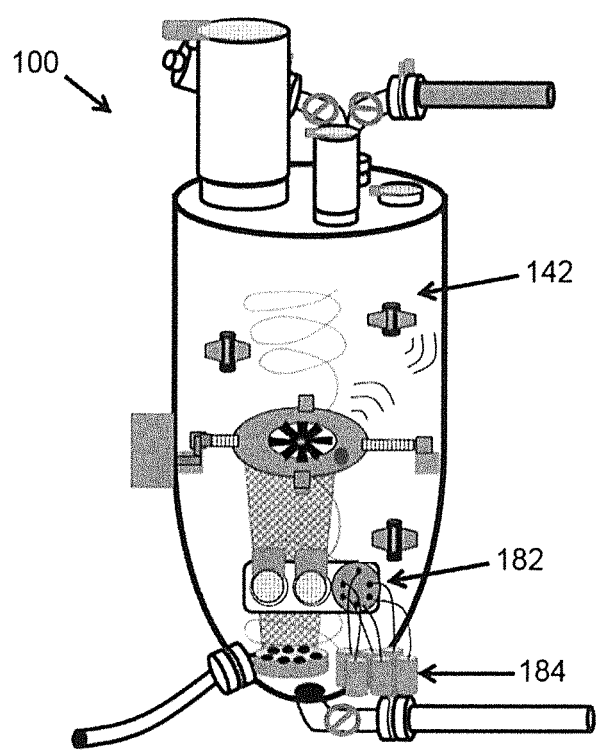

FIG. 2I is a front view of the single-use bioreactor bag 100 where at least one aseptic sampler 184 may be aseptically connected to the aseptic connection port 182. The at least one aseptic sampler 184 may collect fluid samples using manual and/or automated methods. These samples may be removed for further analysis utilizing an external device.

The single-use container 100 of FIGS. 2A-2I is shown as being a bioreactor bag, however it could be any kind of single-use bag, such as a mixing container, a 2D or a 3D bioprocessing bag. FIGS. 3A-3D show different examples of single-use containers that can be combined with insertable components.

FIG. 3A is a side view of an example of a single-use 3D mixing bag 300 which is formed from a film material and contains inlet tubing 304 and outlet tubing 306, aseptic connectors for inserting the devices through transfer containers 310, 312 as well as at least one insertable component 314 that mixes a fluid 308 and at least another insertable component 316 with sensors. FIG. 2B is a front view of a single-use 2D bag 320. FIG. 3C is a side view of a single-use rigid plastic bioreactor assembly 330. FIG. 3D is a side view of a single-use CellSTACK assembly 340 utilized to incubate adherent cells.

It is to be appreciated that the various features shown and described are interchangeable, that is a feature shown in one embodiment may be incorporated into another embodiment. It is further to be appreciated that the methods, functions, algorithms, etc. described above may be implemented by any single device and/or combinations of devices forming a system, including but not limited to personal computers, servers, storage devices, processors, memories, FPGAs, DSPs, etc.

While non-limiting embodiments are disclosed herein, many variations are possible which remain within the concept and scope of the present disclosure. Such variations would become clear to one of ordinary skill in the art after inspection of the specification, drawings and claims herein. The present disclosure therefore is not to be restricted except within the spirit and scope of the appended claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An assembly comprising:
   a single-use sterilizable bag for containing a biological material, the single-use sterilizable bag having at least one insertion opening; and
   at least one insertable component configured to be inserted entirely into the single-use sterilizable bag via the at least one insertion opening and to perform one or more specified tasks with respect to the biological material in the single-use sterilizable bag, wherein the at least one insertable component comprises:
   a positioning unit comprising a dynamic element configured to move the insertable component into a specific position in the single-use sterilizable bag at which the one or more specified tasks is to be carried out;
   a sensing unit and a processing unit for handling the biological material, the processing unit being at least one of a mixing device, a filtration device, an aeration device, a purification device, a centrifugation device and a cell cultivation device that manipulates the biological material in the single-use sterilizable bag to mechanically or chemically modify the biological material; and
   a controlling unit configured to autonomously control all operations of the sensing unit and the processing unit without input from outside the single-use sterilizable bag, wherein the controlling unit controls the processing unit based on whether a measured parameter received from the sensing unit has exceeded a predetermined threshold.

2. The assembly of claim 1, wherein the insertion opening is provided with an aseptic connector configured to enable an aseptic transfer of the at least one insertable component into the single-use sterilizable bag.

3. The assembly of claim 1, wherein the at least one insertable component further comprises a communication unit configured to enable communication between the at least one insertable component and at least one device external to the assembly.

4. The assembly of claim 1, wherein the at least one insertable component is a plurality of insertable components.

5. The assembly of claim 4, wherein at least two of the plurality of insertable components further comprise a communication unit configured to enable communication between the insertable components.

6. The assembly of claim 1, wherein the single-use sterilizable bag further comprises an attachment unit and the at least one insertable component further comprises a connecting unit configured to engage with the attachment unit.

7. The assembly of claim 6, wherein the attachment unit is configured to provide one or more sterile connections for the insertable components to the outside of the assembly.

8. The assembly of claim 1, wherein the positioning unit further comprises at least one static element configured to maintain the insertable component at the specific position to which the insertable component has been moved by the dynamic element.

9. The assembly of claim 8, wherein the static element is a buoyancy device filled with a compressed gas.

10. The assembly of claim 8, wherein the at least one static element comprises at least one buoyancy device that receives compressed gas to hold the insertable component at a specified depth in the biological material in the single-use sterilizable bag.

11. The assembly of claim 1, wherein the positioning unit is configured to position the insertable component autonomously.

12. The assembly of claim 1, wherein the dynamic unit comprises an impeller configured for moving the insertable component.

13. The assembly of claim 1, wherein the insertable component is sterilizable and the single-use sterilizable bag is configured to be sterilized using a first sterilization method.

14. The assembly of claim 13, wherein the insertable component is configured to be sterilized separately from the single-use bag using a second sterilization method, the second sterilization method being different from the first sterilization method.

15. The assembly of claim 13, wherein the insertable component further comprises a body configured to be sterilized using the first sterilization method and at least one compartmentalized container configured to be sterilized using a second sterilization method, and wherein:
   the second sterilization method is different from the first sterilization method;
   the at least one compartmentalized container is configured to enclose an element sensitive to the first sterilization method;
   the at least one compartmentalized container is configured to be embedded in the insertable component after sterilization by being aseptically inserted therein.

16. The assembly of claim 14, wherein the at least one compartmentalized container is configured to be re-used.

* * * * *